United States Patent [19]

Hooven

[11] Patent Number: 4,540,400
[45] Date of Patent: Sep. 10, 1985

[54] NON-INVASIVELY ADJUSTABLE VALVE
[75] Inventor: Michael D. Hooven, Miami, Fla.
[73] Assignee: Cordis Corporation, Miami, Fla.
[21] Appl. No.: 515,700
[22] Filed: Jul. 21, 1983

Related U.S. Application Data

[63] Continuation-in-part of Ser. No. 467,326, Feb. 17, 1983.
[51] Int. Cl.³ .............................................. A61M 27/00
[52] U.S. Cl. ........................................ 604/9; 251/65; 604/247
[58] Field of Search ........................ 604/9.8, 248, 247; 128/748; 251/65; 137/539

[56] References Cited

U.S. PATENT DOCUMENTS

| | | | |
|---|---|---|---|
| 2,879,783 | 3/1979 | Taplin . | |
| 3,495,620 | 2/1970 | Ramondi et al. . | |
| 3,768,508 | 10/1973 | Schulte . | |
| 3,769,982 | 11/1973 | Schulte . | |
| 3,886,948 | 6/1975 | Hakim | 604/9 |
| 3,901,245 | 8/1975 | Spitz et al. . | |
| 3,985,140 | 10/1976 | Harris . | |
| 3,999,553 | 12/1976 | Spitz et al. . | |
| 4,106,510 | 8/1978 | Hakim et al. | 604/9 |
| 4,156,422 | 5/1979 | Hildebrandt et al. | 604/9 |
| 4,332,555 | 6/1982 | Hakim et al. | 604/9 |
| 4,340,038 | 7/1982 | McKean | 128/748 |
| 4,443,214 | 4/1984 | Marion | 604/9 |
| 4,452,423 | 6/1984 | Beblavi | 251/65 |

Primary Examiner—Stephen C. Pellegrino
Attorney, Agent, or Firm—Lockwood, Alex, FitzGibbon & Cummings

[57] ABSTRACT

A non-invasively adjustable intercranial pressure regulator valve and adjustment mechanism therefor which is adapted particularly for the treatment of hydrocephalus and the draining of cerebrospinal fluid (CSF) from a ventricle in the brain to another location in the patient's body. The valve includes a flexible diaphragm which is contacted on both sides by the CSF fluid. A valve seat on the diaphragm is movable with the diaphragm and a ball closure valve is positioned on the cephalad side of the diaphragm. The pressure differential of the CSF fluid across the diaphragm causes the valve seat to flex into and out of engagement with the ball closure valve. The force by which the ball closure valve and valve seat engage each other and, thereby, the pressure differential at which the CSF fluid will drain are adjusted by an adjustment means which includes a magnetic wrench which is both rotatable and longitudinally movable between a first active position in which the wrench may be rotated by a magnet outside of the patient's body to effect adjustment of the ball closure valve and a second inactive position in which the wrench is magnetically locked in its adjusted position.

15 Claims, 5 Drawing Figures

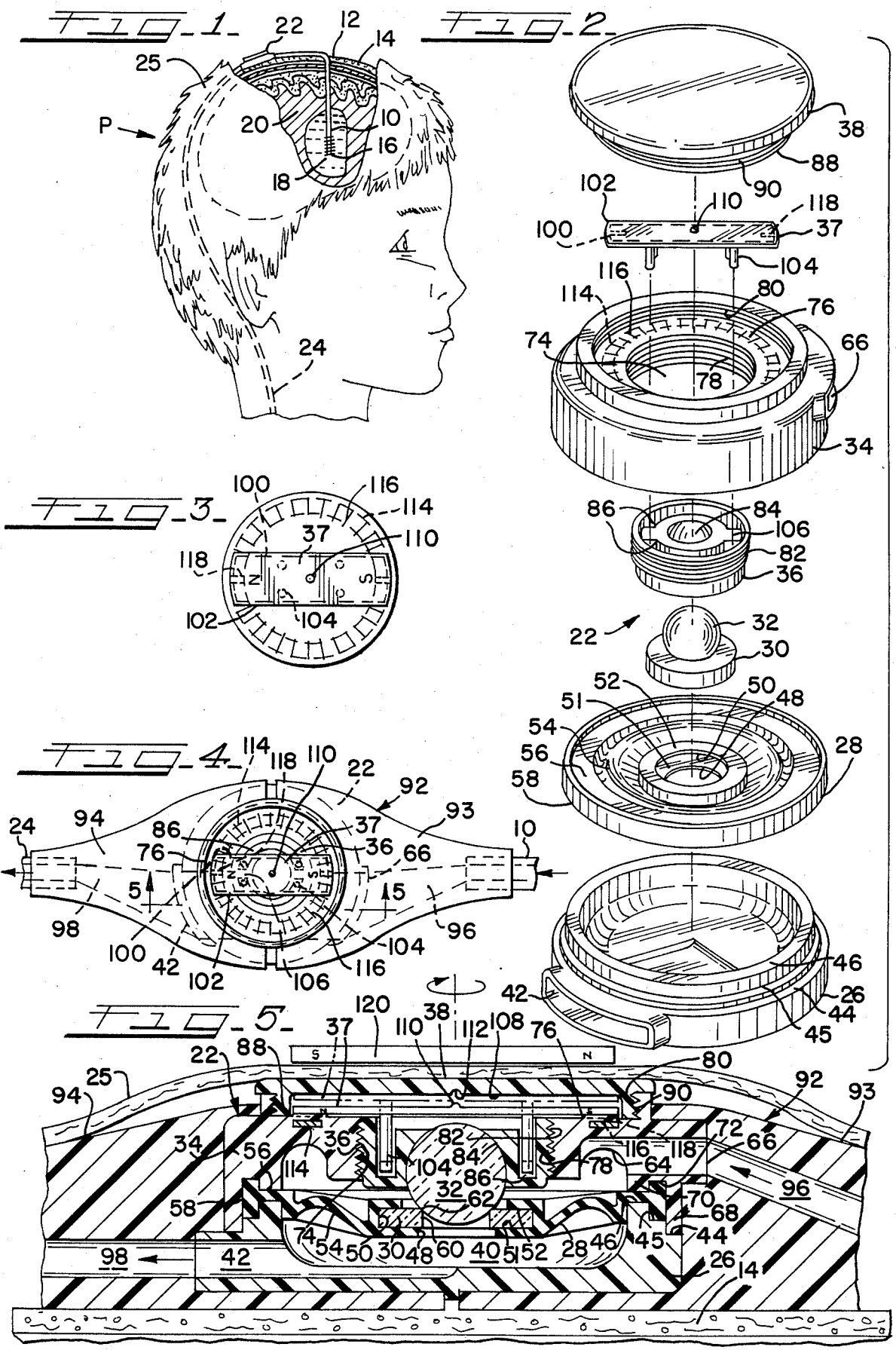

NON-INVASIVELY ADJUSTABLE VALVE

RELATED APPLICATION

This application is a continuation-in-part of application Ser. No. 467,326, filed Feb. 17, 1983.

BACKGROUND AND SUMMARY OF THE INVENTION

The present invention relates to an adjustable valve and, more particularly, to a non-invasively adjustable valve for shunting excess cerebrospinal fluid (CSF) from a ventricle in the brain to another location in the patient's body when the pressure differential between the CSF and the other body fluid reaches a predetermined magnitude, and to an adjustment mechanism therefor.

Hydrocephalus is a condition in which the brain is unable to relieve itself of CSF which collects in the ventricles of the brain. Such CSF, thereby, becomes excessive and results in abnormal ventricular size causing a number of adverse physiological effects including compression of the brain tissue and impairment of the blood flow in the brain tissue and of the brain's normal metabolism.

A variety of CSF regulator valves have been employed in the past for controlling CSF pressure. Such valves include various forms of check valves, servo valves or combinations thereof. One such valve is disclosed in application Ser. No. 467,326, filed Feb. 17, 1983, of which this application is a continuation-in-part.

In the last mentioned valve, a diaphragm containing a valve seat is positioned in the valve casing and both sides of the diaphragm are exposed to the CSF fluid. A ball closure valve is mounted by a threaded screw member in the casing so as to engage the valve seat. The force by which the ball closure engages the valve seat, and thereby, the pressure differential at which the CSF fluid will drain may be adjusted by threading the screw member in or out.

The present invention is directed to an adjustment mechanism for either the aforementioned valve or other valve for the draining of body fluids and a valve containing such adjustment mechanism by which the valve may be non-invasively adjusted trancutaneously from outside of the patient's body. In a valve and adjustment mechanism incorporating the principles of the present invention, a wide range of adjustment of the pressures or pressure differentials at which the valve will drain the fluid is possible. Such adjustment can be performed virtually continuously to enable fine tuning of the valve. A valve and adjustment mechanism incorporating the principles of the present invention is simple in manufacture and operation, and is extremely reliable. A valve and adjustment mechanism incorporating the principles of the present invention may be adjusted with a minimum of torque and minimal possibility of jamming and, once adjusted, the valve and mechanism may be reliably locked in its desired adjustment position.

In one principal aspect of the present invention, adjustment means for a valve which includes a passage in the valve for the flow of fluid through the valve and flow-restricting means for restricting the flow through the passage comprises an elongate rotatable magnet in the valve. The magnet is mounted to the flow restricting means to rotate same to adjust the pressure at which the fluid will flow through the flow restricting means when the magnet is rotated. The magnet is also movable between a first active position and a second inactive position in which the magnet is capable of rotating the flow restricting means to adjust the pressure when the magnet is in its first active position and is incapable of performing such adjustment when in its second inactive position.

In still another principal aspect of the present invention, the aforementioned magnet is longitudinally movable between the first active position and the second inactive position.

In still another principal aspect of the present invention, the aforementioned adjustment means includes valve seat means and valve closure means having screw means and the screw means is engaged by the magnet to rotate the screw means to adjust the force by which the valve closure means engages the valve seat means.

In still another principal aspect of the present invention, the adjustment means includes locking means for locking the magnet against rotation when the magnet is in its second inactive position.

In still another principal aspect of the present invention, the last mentioned locking means may include, either alternatively or in combination, magnetic means which attracts and holds the magnet when the magnet is in its second inactive position and/or detent means on the valve casing and magnet which engage each other.

In still another principal aspect of the present invention, the adjustment means includes pivot means on the valve casing and magnet which is operable when the magnet is in its first active position to cause the magnet to rotate about an axis defined by the pivot means.

In still another principal aspect of the present invention, the aforementioned valve and adjustment means therefor may be a valve for draining cerebrospinal fluid.

In still another principal aspect of the present invention, a valve for the passage of body fluids from one location in the body to another location and the regulation of the pressure of such fluids includes movable means having first and second surfaces of substantial area thereon. First coupling means communicates the area of the first surface with the fluid from the one location and a second coupling communicates the area of the second surface with the other location. Valve seat means on the movable means is movable therewith and includes a passage for the flow of fluid from the first to the second surfaces. Valve closure means is positioned on the side of the movable means adjacent the first surface. The valve closure means is engaged by the movable seat means to close the passage in response to a first lower pressure differential of the fluid acting on the first and second surfaces, and the movable means and its valve seat means are movable away from the valve closure means to open the passage in response to a second higher pressure differential of the fluid acting on the first and second surfaces. Adjustment means includes magnetically rotatable means for selectively rotating one of the valve seat means and valve closure means to adjust the force by which these means engage each other.

In still another principal aspect of the present invention, the aforementioned movable means is a flexible diaphragm.

In still another principal aspect of the present invention, the valve closure means includes mounting means for stationarily mounting the valve closure means such that the valve seat means moves relative to the valve closure means and the adjustment means includes magnetic means coupled to the mounting means for rotating the mounting means.

In still another principal aspect of the present invention, the adjustment means comprises a wrench which includes an elongate rotatable magnet. At least one projection extends from the magnet for engaging one of the valve seat means and valve closure means to rotate same when the magnet is rotated.

In still another principal aspect of the present invention, the adjustment means in the last mentioned valve includes screw means on the valve closure means which is engaged by the wrench to rotate the screw means and valve closure means to adjust the force by which the valve closure means engages the valve seat means.

In still another principal aspect of the present invention, the aforementioned wrench is also longitudinally movable between a first active position and a second inactive position and the wrench is capable of performing the adjustment when in its first active position and is incapable of performing the adjustment when in its second inactive position.

In still another principal aspect of the present invention, the last mentioned adjustment means includes locking means for locking the wrench against rotation when the wrench is in its second inactive position.

In still another principal aspect of the present invention, the last mentioned locking means may include, either alternatively or in combination, magnetic means which attracts and holds the magnet when the wrench is in its second inactive position and/or detent means on a stationary portion of the casing and the wrench which engage each other.

In still another principal aspect of the present invention, the valve may include a stationary casing and pivot means on the casing and aforementioned wrench which is operable, when the wrench is in its first active position, to cause the wrench to rotate about an axis defined by the pivot means.

These and other objects, features and advantages of the present invention will be clearly understood through a consideration of the following detailed description.

BRIEF DESCRIPTION OF THE DRAWING

In the course of this description, reference will frequently be made to the attached drawing in which:

FIG. 1 is illustrative of a hydrocephalus system in which a preferred embodiment of non-invasively adjustable intercranial pressure regulator valve and adjustment mechanism of the present invention may be incorporated;

FIG. 2 is an enlarged, exploded view of a preferred embodiment of non-invasively adjustable valve and adjustment mechanism incorporating the principles of the present invention;

FIG. 3 is a plan view of the wrench and locking portion of a preferred embodiment of adjustment mechanism of the present invention;

FIG. 4 is a reduced, plan view of the assembled valve shown in FIG. 2 as incorporated in the hydrocephalus treatment system shown in FIG.1, but with the cap removed to show the adjustment mechanism; and FIG. 5 is an enlarged, cross-sectioned, partially broken, side elevational view of the valve and adjustment mechanism as viewed substantially along line 5—5 in FIG. 4.

DESCRIPTION OF THE PREFERRED EMBODIMENT

In FIG. 1 a hydrocephalus system incorporating the principles of the present invention is illustrated. The system shown includes a ventricular catheter 10 which is inserted through an opening 12 which has been formed in the skull 14 of the patient P who is to undergo the hydrocephalus treatment. The catheter 10 is preferably radiopague. The distal end 16 of the ventricular catheter 10 is positioned in a ventricle 18 in the patient's brain tissue 20 in which the CSF accumulates. The other end of the catheter 10 is coupled to the non-invasively adjustable intercranial pressure regulator valve 22 of the present invention, as shown in FIG. 1, and a drain catheter 24 is coupled to the valve 22 to receive the discharge from the valve to drain the CSF discharge to another location in the patient's body, such as the right atrium of the patient's heart (not shown). The valve 22, the portion of the ventricular catheter 10 exterior to the skull 14, and the drain catheter 24 are preferably located between the patient's skull 14 and scalp 25, as shown in FIG. 1.

The details of the valve 22 are best shown in FIGS. 2–5. As shown in FIG. 2, the preferred embodiment of noninvasively adjustable regulator valve incorporating the principles of the present invention includes a valve casing bottom 26, a flexible diaphragm 28, a valve seat 30 and valve closure ball 32, a valve casing top 34, a threaded screw member 36, an adjustment wrench 37, and a casing closure cap 38. The diaphragm 28, valve seat 30 and closure ball 32 together define flow restricting means for restricting the flow of fluid through the valve. The casing bottom 26, casing top 34, screw member 36 and closure cap 38 are formed of a suitable durable, biologically compatible material, such as thermoplastic polymers of polyethersulfone or polycarbonates.

The valve casing bottom 26 comprises a substantially cup shaped member which defines, as shown in FIG. 5, a fluid discharge chamber 40 having a discharge port 42 of preferably elongate cross-section as shown in FIG. 2. The upper rim of the casing bottom 26 is formed with a plurality of stepped raised shoulders 44, 45 and 46.

The diaphragm 28 comprises a preferably substantially circular, flexible movable disc having a fluid flow passage 48 adjacent its center. An annular groove 50 is formed in the diaphragm adjacent the flow passage 48 to receive and hold the valve seat 30 as shown in FIG. 5. The groove 50 is defined by a lower flange 51 and an upper flange 52, the upper flange 52 being preferably somewhat shorter than the lower flange 51 to accommodate unrestricted movement of the diaphragm and valve seat 30 relative to the valve closure ball 32 during operation of the valve. The lower flange 51 is surrounded by an annular disc portion 54 which is preferably convoluted when installed in the casing, as shown in FIG. 5. The convolution provides increased flexibility of the diaphragm and stability against cocking during operation. A horizontal annular flange 56 surrounds the annular disc portion 54. The annular flange 56 is encircled by a generally vertical annular flange 58 to complete the diaphragm construction. The diaphragm 28 may be formed of any durable, flexible, biologically compatible material, such as Silastic rubber.

The valve seat 30 is preferably circular, as shown in FIGS. 2 and 5, and includes an opening 60 through its center to provide for the passage of fluid through the diaphragm. As shown in FIG. 5, a suitable shoulder 62 is formed at the top of the opening 60 in valve seat 30 to engage the valve closure ball 32 to form a seal with the ball 32 to block passage of the fluid through the opening 60.

The valve closure ball 32 is positioned on the cephalad side of the diaphragm and is preferably substantially spherical in shape, as shown in FIGS. 2 and 5, although it will be understood that other shapes may be satisfactorily employed in the present invention. As shown in FIG. 5, valve closure ball 32 is solid, although it may be hollow, if desired.

Both the valve seat 30 and valve closure ball 32 are also formed of a durable yet biologically compatible material. By way of example, sapphire may be used as a material to form the valve seat and ball.

The valve casing top 34 also comprises a substantially cup shaped member which defines, as shown in FIG. 5, an inlet chamber 64 and an inlet port 66, the latter of which is also of elongate oblong cross-section, as best seen in FIG. 2. The casing top 34 includes, as best shown in FIG. 5, a pair of downwardly extending annular flanges 68 and 70 with flange 68 being somewhat longer than flange 70. Flanges 68 and 70 are spaced from each other to define a groove 72 therebetween. The diameter and width of flange 70 are preferably substantially equal to the diameter and width of shoulder 46 on the casing bottom 26 and overlies that shoulder when the casing is assembled, as shown in FIG. 5. The diameter and width of groove 72 are substantially equal to the diameter and width of shoulder 45 on the casing bottom and overlies that shoulder when the casing is assembled, as shown in FIG. 5. The vertical annular flange 58 of the diaphragm 28 is clamped between the groove 72 and shoulder 45 and the horizontal annular flange 56 of the diaphragm is clamped between the flange 70 and shoulder 46 when the valve casing is assembled, as shown in FIG. 5. The valve casings and diaphragm, thereby, fit snugly together when assembled and they are all secured together by suitable means such as solvent, adhesive or ultrasonic bonding.

An opening 74 extends through the top of the top valve casing 34. The opening is preferably stepped at 76 and the wall of the opening is threaded with two sets of threads 78 and 80.

The screw member 36 contains external threads 82 on its outside surface which are adapted to be threaded into the threads 78 in the opening 74 of the casing top. The ball 32 is attached in a recess 84 in the screw member 36 by suitable means, such as insert molding. The ball 32 is, therefore, stationarily mounted to the screw member. A pair of arcuate slots 86 are also formed in the screw member, as shown in FIG. 2, and comprise part of the adjustment mechanism to be described in more detail to follow.

The closure cap 38 includes a downwardly extending annular flange 88 which contains threads 90 on its external surface so that the cap may be threaded onto the threads 80 for closure of the opening 74 in the casing top 34.

Once the lower and upper valve casings 26 and 34, the diaphragm 28, the valve seat 30, the ball 32 and the screw member 36 have been assembled together, a flexible outer housing is preferably assembled over the the valve casing by sliding the outer housing over the valve casing. The wrench 37 and cap 38 may then be installed.

The flexible outer housing 92, as shown in FIGS. 4 and 5, is preferably formed by a pair of housing half members 93 and 94, as shown in FIGS. 4 and 5. Housing half member 93 includes a tapering inlet antechamber 96 which, at its wider end, communicates with the inlet port 66 and at the other narrower end with the ventricular catheter 10. The other housing half member 94 also includes a tapered discharge antechamber 98 which, at its wider end, communicates with the discharge port 42 and at the other narrower end with the drain catheter 24, as best seen in FIG. 4. The outer housing 92 is formed of a flexible, biologically compatible material, such as Silastic rubber.

The closure cap 38 is preferably exposed through the housing 92, as shown in FIG. 5, to allow access to the interior of the valve, if necessary.

The operation of the valve thus far described is as follows:

The CSF in the ventricle 18 which is to be drained communicates with the valve via the ventricular catheter 10, the inlet antechamber 96 in the housing half member 93, the inlet port 66 and the inlet chamber 64. Thereby, the pressure of this CSF will act upon substantially the entire upper surface of the diaphragm 28 which is of substantial area as may be seen in FIG. 5. So long as the pressure of the fluid on the discharge side of the valve which is also acting upon the entire lower surface of the diaphragm 28 is substantially equal to the pressure of the CSF acting upon the upper surface of the diaphragm, the resilient nature of the diagraphm will cause it to flex upwardly, as viewed in FIG. 5, and cause the valve seat 30 to engage the stationary valve closure ball 32 to close the passages 48 and 60 through the diaphragm and valve seat and prevent flow of the fluid through these passages.

When a pressure increase occurs in the CSF in the ventricle, this increased pressure will be transmitted to the upper surface area of the diaphragm 28. When the pressure differential increases between the upper surface area of the diaphragm and the fluid in the discharge chamber 40 which exerts its pressure against the bottom surface area of the diaghragm, the diaphragm will begin to flex downwardly in response to this increased differential in pressure. Such flexing will cause the valve seat 30 to move away from the stationary closure ball 32 and allow CSF to pass between the upper surface of the diaphragm from chamber 64 through the passages 48 and 60 to the discharge chamber 40 and the lower surface of the diaphragm. This fluid will be discharged through the discharge port 42, discharge antichamber 98 and discharge catheter 24. The discharge of CSF through passages 48 and 60 will continue until the pressure differential between the upper and lower surfaces of the diaphragm returns to a predetermined low differential causing the diaphragm to again flex upwardly until the valve seat 30 engages the valve closure ball 32 to close the passages 48 and 60.

As previously mentioned, the pressure differential at which the valve opens to permit the drainage of CSF may be readily non-invasively adjusted by the adjustment mechanism of the present invention.

The preferred embodiment of adjustment mechanism of the invention includes the spanner wrench 37 which is installed through the top of the casing top 34. The wrench 37 includes an elongate magnet 100 having north and south poles. The magnet 100 is preferably encapsulated in a biologically compatible coating 102, as shown in FIGS. 2-4, in order to prevent contact of the CSF with the magnetic material. A plurality of projections, for example elongate spaced pins 104, extend downwardly from the wrench 37 and the coating 102. The pins 104 may be integrally formed with the coating 102 by way of molding the pins simultaneously with the coating. The pins 104 preferably extend downwardly into the arcuate slots 86 in the screw member 36 and straddle bridging portions 106 which separate the slots from each other, as best seen in FIGS. 2 and 4.

The annular flange 88 on the cap 38 extends downwardly a sufficient distance to define a recess 108, as best seen in FIG. 5. The recess 108 is of sufficient depth to allow movement of the spanner wrench 37 between a lower inactive position, as shown in solid in FIG. 5, and an upper active position, as shown in dot and dash in FIG. 5. When the spanner wrench 37 is in its upper active position, a small pivot projection 110, which is also preferably integrally cast in the coating 102 of the wrench 37, extends upwardly and into a complementary recess 112 in the underside of the cap 38 to define a pivot axis for rotation of the wrench, as will be discussed in more detail to follow. When the wrench is in its upper active position, as shown in dot and dash in FIG. 5, the pins 104 are drawn upward in the arcuate slots 86. However, the pins are of sufficient length so that they continue to remain in the arcute slots 86 as shown in FIG. 5.

As best seen in FIGS. 3–5, an annular metallic ring 114 is also positioned at the step 76 in the casing top 34. The ring 114 is preferably formed of a ferro-magnetic material and, to prevent contact with the CSF or other bodily fluids, it is also preferably encapsulated, such as by molding into the material from which the casing top 34 is formed, as shown in FIG. 5.

The upwardly facing surface of the step 76 is also preferably formed with a plurality of radially extending grooves or slots 116 and the underside of the spanner wrench 37 which overlies the grooves or slots 116 may include complementary ribs or ridges 118 which are adapted to engage given slots on step 76 when the wrench 37 is in its lower inactive position, as shown in solid in FIG. 5. Thereby, the slots 116 and ribs 118 provide a detent construction which assists in locking the wrench 37 in its desired adjustment position and further resists rotation of the wrench in that position. It will be understood that instead of the slots 116 and ribs 118, other constructions may be relied upon to resist such rotation, such as roughening or serration of the under surface of the wrench 37 and the upwardly facing surface of the step 76.

Although adjustment of the valve and adjustment mechanism should be clear from the foregoing description of the adjustment mechanism, a brief description of a preferred manner of adjustment will be described to follow.

It will be assumed that the valve 22 and its adjustment mechanism has previously been installed beneath the patient's scalp 25 and that it is now desired to non-invasively readjust the valve.

At this time the spanner wrench 37 will be in its lower inactive position, as shown in solid in FIG. 5. This is because it is automatically drawn down into this position by virtue of the magnetic attraction between the magnet 100 and the ring 114. Such magnetic attraction will automatically lock the wrench against rotation and such locking is further enhanced by the fact that if any slight rotation of the wrench 37 occurs whatsoever, its ribs 118 will engage the closest adjacent grooves 116.

In order to adjust the valve, all that is necessary is to place another elongate magnet 120, as shown in FIG. 5, in overlying relationship to the wrench 37 on the outside of the scalp 25 and rotate the magnet 120. The magnet 120 should be sized to create a stronger magnetic attraction to the magnet 100 in the wrench than the magnetic attraction between the magnet 100 and the ring 114. As such, when the magnet 120 is positioned, it will overcome the attraction of the magnet 100 to the ring 114 and the wrench 37 will be attracted upwardly into its active position, as shown in dot and dash in FIG. 5. When the wrench 37 has moved to its active position, pivot projection 110 will enter pivot recess 112 to define the pivot axis about which the wrench is to rotate.

When the magnet 120 is now rotated, it will cause the wrench 37 and its magnet 100 to rotate in the same direction. The pins 104, which are an integral part of the wrench 37, will bear against the bridging portions 106 which separate the arcuate slots 86 in the screw member 36 to cause the screw member to either thread upwardly or downwardly, depending upon the direction of rotation of the magnet 120. If the screw member 36 is rotated to move downwardly, its valve closure ball 32 will engage the valve seat 30 with a greater force, thus resulting in an increase in the pressure differential in the CSF fluid before the valve opens. Conversely, if the screw member 36 is rotated to move upwardly, the force with which its valve closure ball 32 will bear against the valve seat 30 will decrease resulting in a decrease in the CSF pressure differential which is necessary to operate the valve.

Once the desired adjustment is attained, all that is necessary is to remove the magnet 120 from the patient's scalp 25. When this occurs, the magnetic attraction to the magnet 100 of the wrench 37 disappears and the magnet 100 will again be attracted to the ring 114 causing the wrench 37 to drop to its inactive position, as shown in solid in FIG. 5. In this position, the wrench is not only locked in its desired adjustment position by virtue of the magnetic attraction between its magnet 100 and ring 114, but is also prevented from rotating due to the engagement of its ribs 118 in grooves or slots 116 in the step 76 of the casing top 34.

Because the wrench 37 is firmly locked in its lower inactive position, the threads 74 and 78 may be virtually frictionless threads because friction between these threads is not needed to maintain the adjustment position of the valve. Due to this essentially frictionless operation of the threads and because of the pivot action provided by projection 110 in recess 112, adjustment may be performed with a minimum of torque and possibility of jamming. Moreover, it will be readily seen that a wide range of adjustments are possible in a valve having the adjustment mechanism of the present invention and these adjustments may be accomplished virtually continuously over that range to allow fine tuning of the valve non-invasively of the patient.

It will also be seen that the valve and adjustment mechanism of the present invention may be of extremely small size, are simple to manufacture and operate, and are extremely reliable.

Although the present invention has been shown in a system for draining a ventricle in the brain tissue of a patient, it will be understood that the valve and adjustment mechanism of the present invention may be readily employed in the control and regulation of the pressure of various other body fluids from and to various other body cavities of the patient. By way of example, the invention may be employed in the draining and regulation of spinal or other fluids of the patient.

It will also be understood that the embodiment of the present invention which has been described is merely illustrative of one of the applications of the principles of the present invention. Numerous modifications may be made by those skilled in the art without departing from the true spirit and scope of the invention.

What is claimed is:

1. A valve for regulating the passage of body fluids from one location in the body to another location, comprising:
    a housing;
    means including a flexible diaphragm within said housing for dividing the interior thereof into first and second interior chambers, said diaphragm including a central portion having a position within said diaphragm dependent on the fluid pressure differential between said chambers;
    an inlet port for admitting fluid from said one location into said first interior chamber;
    a discharge port for discharging fluid from said second interior chamber to said another location;
    a valve seat mounted on said central portion of said diaphragm for movement therewith, and having a passageway opening from said first interior chamber to said second interior chamber;
    valve closure means within one of said chambers arranged to restrict the flow of fluid through said passageway in response to the position of said valve seat within said housing to maintain a predetermined fluid pressure differential between said first and second interior chambers, said predetermined pressure differential being dependent on the position of said valve closure means within said housing; and
    adjusting means responsive to an externally applied magnetic field for adjusting the position of said valve closure means within said housing to vary said predetermined pressure differential.

2. A valve as defined in claim 1 wherein said adjusting means include a magnetic member mounted for movement in response to application of said magnetic field and coupled to said valve closure means such that movement of said magnetic member changes the position of said valve closure means within said housing to adjust said predetermined pressure differential.

3. A valve as defined in claim 2 wherein said valve closure means are carried on a screw member rotatably mounted to said housing such that rotation of said screw member relative to said housing changes the position of said valve closure means relative to said valve seat.

4. A valve as defined in claim 3 wherein said magnetic member comprises an elongate magnetic wrench mounted for rotation within said housing under the influence of said magnetic field and coupled to said screw member for rotating said screw member upon rotation of said magnetic wrench.

5. A valve as defined in claim 4 wherein said screw member is threaded and engages complementary threads formed in said housing such that said screw member moves toward said valve seat in response to rotation in one direction and moves away from said valve seat upon rotation in the opposite direction.

6. A valve as defined in claim 5 wherein said valve further comprises locking means responsive to application of said magnetic field for preventing rotation of said screw member in the absence of said magnetic field and for permitting rotation of said screw member when said magnetic field is applied.

7. A valve as defined in claim 6 wherein said locking means include a metallic magnetic member mounted in said housing for magnetically biasing said magnetic wrench into contact with said housing in the absence of said magnetic field to prevent relative movement between said magnetic wrench and said housing.

8. A valve as defined in claim 1 wherein said valve further comprises locking means responsive to application of said magnetic field for preventing adjustment of the position of said valve closure member in the absence of said magnetic field.

9. A valve for regulating the passage of body fluids from one location in the body to another location, comprising:
    a housing;
    means including a flexible diaphragm within said housing for dividing the interior thereof into first and second interior chambers, said diaphragm including a central portion having a position within said housing dependent on the fluid pressure differential between said chambers;
    an inlet port for admitting fluid from said one location into said first interior chamber;
    a discharge port for discharging fluid from said second interior chamber to said another location;
    a valve seat mounted on said central portion of said diaphragm for movement therewith, and having a passageway opening from said first interior chamber to said second interior chamber;
    valve closure means threadedly mounted within one of said chambers arranged to restrict the flow of fluid through said passageway in response to the position of said valve seat within said housing to maintain a predetermined fluid pressure differential between said first and second interior chambers, said predetermined pressure differential being dependent on the position of said valve closure means within said housing;
    adjusting means responsive to an externally applied magnetic field for rotating said valve closure means to adjust the position of said valve closure means within said housing to vary said predetermined pressure differential; and
    locking means responsive to application of said magnetic field to said adjusting means for preventing adjustment of said predetermined pressure differential in the absence of said magnetic field and for permitting said adjustment upon application of said magnetic field.

10. A valve as defined in claim 9 wherein said adjusting means include a magnetic member mounted for rotation in response to application of said magnetic field and coupled to said valve closure means such that rotation of said magnetic member changes said position of said valve closure means within said housing to adjust said predetermined pressure differential.

11. A valve as defined in claim 10 wherein said valve closure means are carried on a screw member rotatably mounted to said housing such that rotation of said screw member relative to said housing changes said position of said valve closure means relative to said valve seat.

12. A valve as defined in claim 11 wherein said magnetic member comprises an elongate magnetic wrench mounted for rotation within said housing under the influence of said magnetic field and coupled to said screw member for rotating said screw member upon rotation of said magnetic wrench.

13. A valve as defined in claim 12 wherein said valve closure means is threaded and engages complementary threads formed in said housing such that said closure means moves toward said valve seat in response to rotation in one direction and moves away from said valve seat upon rotation in the opposite direction.

14. A valve as defined in claim 13 wherein said locking means include a metallic member mounted in said housing for magnetically biasing said magnetic wrench into contact with said housing in the absence of said magnetic field to prevent relative movement between said magnetic wrench and said housing.

15. A valve as defined in claim 14 wherein said metallic member comprises a metallic annular ring and said housing includes a serrated surface adjacent said ring for engaging said magnetic wrench to prevent relative movement therebetween in the absence of said magnetic field.

* * * * *